(12) United States Patent
Matsui

(10) Patent No.: US 7,755,751 B2
(45) Date of Patent: Jul. 13, 2010

(54) OPTICAL INSPECTION METHOD AND OPTICAL INSPECTION APPARATUS

(75) Inventor: Shigeru Matsui, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 401 days.

(21) Appl. No.: 11/819,712

(22) Filed: Jun. 28, 2007

(65) Prior Publication Data

US 2008/0002194 A1    Jan. 3, 2008

(30) Foreign Application Priority Data

Jun. 30, 2006   (JP)   ............... 2006-180632

(51) Int. Cl.
*G01N 21/00* (2006.01)
(52) U.S. Cl. ................. 356/237.2; 356/237.3
(58) Field of Classification Search .... 356/237.1–237.5
See application file for complete search history.

(56) References Cited

U.S. PATENT DOCUMENTS 5,798,829 A       8/1998   Vaez-Iravani
6,084,716 A  *    7/2000   Sanada et al. ............... 359/629

FOREIGN PATENT DOCUMENTS

JP      2001-255278      9/2001

* cited by examiner

*Primary Examiner*—Michael P Stafira
(74) *Attorney, Agent, or Firm*—McDermott Will & Emery LLP

(57) ABSTRACT

In the conventional contaminant particle/defect inspection method, if the illuminance of the illumination beam is held at not more than a predetermined upper limit value not to give thermal damage to the sample, the detection sensitivity and the inspection speed being in the tradeoff relation with each other, it is very difficult to improve one of the detection sensitivity and the inspection speed without sacrificing the other or improve both at the same time. The invention provides an improved optical inspection method and an improved optical inspection apparatus, in which a pulse laser is used as a light source, and a laser beam flux is split into a plurality of laser beam fluxes which are given different time delay to form a plurality of illumination spots. The scattered light signal from each illumination spot is isolated and detected by using a light emission start timing signal for each illumination spot.

34 Claims, 9 Drawing Sheets

OPTICAL INSPECTION METHOD AND OPTICAL INSPECTION APPARATUS

BACKGROUND OF THE INVENTION

This invention relates to an optical inspection method and an optical inspection apparatus for detecting a contaminant particle or a defect of a sample to be inspected, such as a thin film substrate, a semiconductor substrate or a photomask by radiating light thereon, or in particular to an optical inspection method and an optical inspection apparatus having a sensitivity or a throughput improved as compared with the conventional method and apparatus.

In the production line of a semiconductor substrate or a thin film substrate, the inspection is conducted for contaminant particles attached on the surface of the semiconductor substrate or the thin film substrate to monitor the dust generation in the manufacturing equipment. In the semiconductor substrate before forming a circuit pattern, for example, the detection of fine contaminant particles or micro defects on the order of not more than several tens of nm on the surface thereof is required. A conventional technique for detecting fine defects on the surface of a sample such as a semiconductor substrate is described in, for example, U.S. Pat. No. 5,798,829, in which a focused laser light flux is fixedly radiated on the surface of the semiconductor substrate (the illuminated area formed on the semiconductor substrate surface by the laser light flux radiated is called an illumination spot), and the scattered light generated from a contaminant particle, if any, attached on the semiconductor substrate is detected while rotating and translating the semiconductor substrate so that the whole surface of the semiconductor substrate is inspected for a contaminant particle or defect. For detecting the scattered light, an ellipsoidal mirror is used. The detection position on the semiconductor substrate is defined a primary focus position of the ellipse and the light-receiving surface of a photodetector is arranged at a secondary focus position. In this way, the scattered light generated from a contaminant particle is focused at a wide solid angle to detect even a fine contaminant particle. In this conventional technique, only one laser light flux for illuminating the semiconductor substrate corresponds to one incident angle, and only one illumination spot is formed on the semiconductor substrate surface by the particular laser light flux.

Another conventional technique is described in, for example, JP-A-2001-255278, in which a condenser lens and a photodetector are arranged at combined positions of a plurality of elevation angles and azimuthal angles with respect to the surface of the semiconductor substrate, and the scattered light focused by each condenser lens is detected by the photodetector, so that a fine contaminant particle can be detected in an advantageous direction conforming with the three-dimensional radiation distribution characteristic of the scattered light from the particular fine contaminant particle. In this prior art, although two laser light fluxes for illuminating the semiconductor substrate exist for oblique and normal illumination, only one laser light flux corresponds to one incident angle and also only one illumination spot is formed on the semiconductor substrate surface by the particular laser light flux.

With the semiconductor substrate (semiconductor wafer), the thin film substrate and the photomask, the size of the contaminant particle or defect requiring detection is sharply reduced with the increase in package density. In the case where the particle size of the contaminant particle is so small as to follow the Rayleigh scattering, the scatter signal amount S obtained by the photodetector detecting the scattered light from the contaminant particle to be detected on a flat, smooth sample surface is generally proportional to the value of the right side of the following equation:

$$S \propto (\text{illuminance of illumination beam}) \times (\text{size of contaminant particle to the power of 6}) \times (\text{illumination wavelength to the power of } -4) \times (\text{collection efficiency of scattered light detection optics}) \times (\text{duration of scattered light}) \times (\text{quantum efficiency of photodetector}) \times (\text{gain of photodetector})$$

where the noise level N for detection is generally substantially proportional to the value of the right side of the following equation:

$$\text{Square root of } N \propto (\text{illuminance of illumination beam}) \times (\text{area of illumination spot}) \times (\text{scattering efficiency of sample surface})$$

The following factors, therefore, have so far been well known to improve the detection sensitivity of contaminant particles or defects:

(1) The illuminance of the illumination beam in the illumination spot is increased to increase the strength of the scattered light.

(2) The wavelength of the illumination beam is shortened to increase the strength of the scattered light.

(3) The numerical aperture of the focusing optics is increased to increase the efficiency of focusing the scattered light.

(4) The performance of the photodetector such as quantum efficiency and S/N is improved.

(5) The background scattering is reduced by reducing the area of the illumination spot.

(6) The primary scanning rate of the sample stage is reduced to lengthen the time for the contaminant particle or defect to pass through the illumination spot.

(7) The diameter of the illumination spot along the primary scanning direction is increased to lengthen the time for a contaminant particle or defect to pass through the illumination spot.

Under the circumstances, however, it is not easy to improve the sensitivity even if these measures are taken, for the reasons described below.

(1) An increased illuminance of the illumination beam causes the surface of the sample to absorb the energy of the illumination beam and increases the surface temperature of the sample thereby increasing the risk of thermal damage to the sample.

(2) The wavelength of the available light source having an output suitable for detecting a contaminant particle or defect is limited and cannot be shortened to less than a certain limit.

(3) The collection efficiency of the scattered light emitted from contaminant particles or defects fails to reach more than 100%. The figure is generally about 50% in the prior art, and this value cannot be doubled in the future.

(4) In the prior art, the quantum efficiency and S/N of the photomultiplier tube used as a photodetector suitable for detecting weak scattered light have almost reached a theoretical limit and a further improvement thereof is not expected.

(5) The area of the illumination spot can be effectively reduced at the sacrifice of a lengthened time required to inspect the whole surface of the sample to be inspected.

(6) A lower primary scanning rate, like in (5), leads to the disadvantage of a longer time required to inspect the whole surface of the sample.

(7) The mere increase in the diameter of the illumination spot along the primary scanning direction is not effective as it is offset by the increased background scattering due to the increased area of the illumination spot, while a decreased diameter of the illumination spot along the direction orthogonal to the primary scanning direction to prevent the illumination spot area from increasing, on the other hand, like in (5), disadvantageously lengthens the time required for inspection of the whole surface of the sample.

SUMMARY OF THE INVENTION

In view of this situation, the object of this invention is to provide an optical inspection method and an optical inspection apparatus in which the detection sensitivity of contaminant particles or defects is improved without sacrificing the time required to inspect the whole surface of the sample, the time required for inspection of the whole surface of the sample is reduced without sacrificing the detection sensitivity of contaminant particles or defects, and both the detection sensitivity of contaminant particles or defects and the time required for inspection of the whole surface of the sample are improved. This invention is intended to provide a technique for achieving this object.

In order to achieve the object described above, according to this invention, there is provided an optical inspection apparatus comprising a means for forming not one but a plurality of illumination spots by radiating the illumination beam on the surface of the sample in order to generate and detect the scattered light from a contaminant particle or a defect on the sample surface and detecting by isolating the scattered light signal generated from the plurality of the illumination spots for each scattered light generated from each illumination spot. More specifically, there is provided an optical inspection apparatus comprising a sample stage for moving a sample in accordance with a predetermined pattern, an illumination means for radiating the light from a light source on the surface of the sample, and a light detection means for detecting the light generated by the radiation of the illumination beam on the sample, wherein the illumination means includes a means for splitting a single light flux generated from the light source into a plurality of light fluxes and forming a plurality of illumination spots in such a manner as to superpose at least a part of the loci plotted by the illumination spots generated in predetermined spaced relation with each other on the sample by the illumination means radiating the plurality of split light fluxes during the movement of the sample on the sample stage, and an optical signal isolation/detection means for detecting by isolating the signal detected at different time points by the light detection means from the light generated at the same position on the sample from the plurality of the illumination spots. There is also provided an optical inspection method implemented by the aforementioned optical inspection apparatus. The light source may be either a CW light source or a pulse light source for radiating the light intermittently. To facilitate the timing adjustment for synthesizing the detected light, however, the pulse light source is more preferable. This is by reason of the fact that the optical signal generated with the passage of the same position of the sample through the plurality of illumination spots is obtained from the photodetector, and the light emission timing of the pulse light emission can be used as a timing signal to synthesize the information for the same position. In the case of the CW light source, the timing signal for synthesis can be calculated based on the speed of the sample stage. In this method, the same point on the sample is inspected twice, and therefore, the inspection sensitivity can be improved. Also, the areas irradiated with the plurality of illumination spots on the sample are arranged not to be superposed one on another with the movement of the sample stage thereby to improve the throughput. Also in this case, the light emission timing of the pulse laser can be used to separate the optical signal information from the plurality of illumination spots. The layout patterns of the plurality of illumination spots can be large in number as described in the embodiment later, and each layout pattern can produce a unique effect. The photodetector is preferably a photomultiplier tube having a high response speed. Depending on the moving speed of the sample stage, however, an ordinary optical element such as a CCD can be used.

According to this invention, the detection sensitivity of contaminant particles or defects can be improved without sacrificing the time required for inspecting the whole surface of the sample, or the time required for inspecting the whole surface of the sample can be improved without sacrificing the detection sensitivity of contaminant particles or defects. Further, both the detection sensitivity of contaminant particles and defects and the time required for inspecting the whole surface of the sample can be improved at the same time.

Other objects, features and advantages of the invention will become apparent from the following description of the embodiments of the invention taken in conjunction with the accompanying drawings.

DESCRIPTION OF THE INVENTION

This invention is explained in detail below.

Figure 1A:
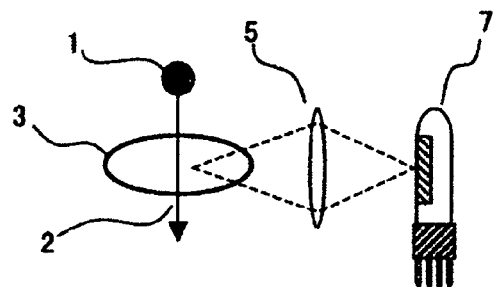
FIGS. 1A, 1B, 1C are diagrams for explaining the effect of producing a plurality of illumination spots and arranging a plurality of photodetectors.
Figure 1B:
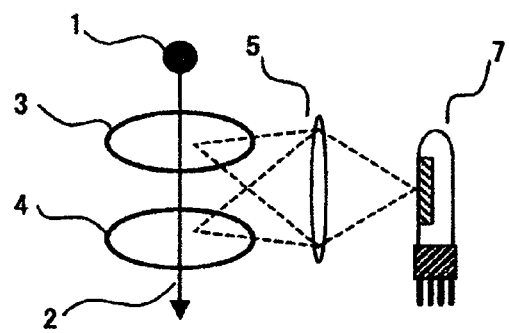
Figure 1C:
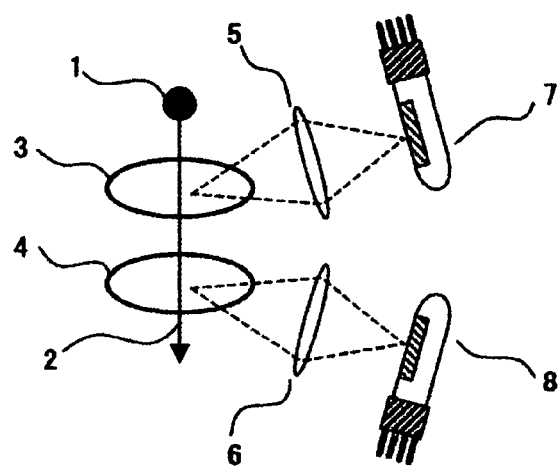

The configuration in which the scattered light generated from a single illumination spot is detected by a single photodetector as in the prior art is shown in FIG. 1A. A sample is mounted on a sample stage. The sample stage moves in a combination of a translation movement for primary scanning and another translation movement in the direction orthogonal to the first translation for secondary scanning or a combination of the rotational movement for primary scanning and the translation movement for secondary scanning. A contaminant particle 1 on the surface of the sample is moved along a locus 2 by the primary scanning of the sample stage. The contaminant particle 1, upon passage through an illumination spot 3 on the locus 2, generates the scattered light by the radiated light. This scattered light is condensed by a scattered light condenser lens 5, and detected and converted into a scattered light signal by a photodetector 7. Next, the configuration in which two illumination spots 3, 4 are arranged in juxtaposition not to be superposed one on the other along the direction of primary scanning of the sample stage and the scattered light generated from the two illumination spots are detected by a single photodetector 7 is shown in FIG. 1B. In the configuration of FIG. 1B, the contaminant particle 1, after passing through a first illumination spot 3, passes through a second illumination spot 4, and therefore, two scattered light signals are obtained from the photodetector 7. In the configuration of FIG. 1B, the sum of these two scattered light signals is calculated as a total scattered light signal. Further, the configuration in which two illumination spots 3, 4 are juxtaposed in a manner not to be superposed one on the other along the direction of primary scanning of the sample stage and two photodetectors 7, 8 detect the scattered light generated from the two different illumination spots, respectively, is shown in FIG. 1C. In the configuration of FIG. 1C, the contaminant particle 1 passes, after passing through the first illumination spot 3, passes the second illumination spot 4, and therefore, two scattered light signals from the first and second photodetectors 7, 8 can be obtained. In the configuration of FIG. 1C, the sum of these two scattered light signals is calculated as a total scattered light signal.

In FIGS. 1A to 1C, the size and area of the illumination spots, the illuminance of the radiated light in the respective illumination spots and the collection efficiency of the condenser lenses 5, 6 are assumed to be identical with each other. In the configuration of FIGS. 1A to 1C, S/N of the total scattered light signal detected by moving the same contaminant particle 1 on the same sample stage at the primary scanning speed is compared as a value relative to S/N of the scattered light signal obtained in the configuration of FIG. 1A as unity. In the configuration of FIG. 1B, the size of the total scattered light signal is twice that of FIG. 1A. Also, in FIG. 1B, the background scattered light is generated from two illumination spots equivalent to FIG. 1A, and detected by a single photodetector 7, resulting in the background scattered light strength twice as large as in FIG. 1A. As described earlier, the noise increases substantially in proportion to the square root of the background scattered light strength, and therefore, the noise in FIG. 1B is about $\sqrt{2}$ times as large as in FIG. 1A for each scattered light signal. In the case where the noise characteristic has no temporal correlation, the addition of two measurements of the signal containing the noises leads to the average value (expected value) of the noise contained in the measurement not double but $\sqrt{2}$ times due to the averaging effect. Therefore, the size of the noise contained in the result of adding two scattered light signals is twice that of FIG. 1A. As a result, the relative value of S/N of FIG. 1B with S/N of FIG. 1A as unity is nothing but unity equivalent to that of FIG. 1A due to the fact that the total scattered light signal is twice as large and so is the noise. Next, in the configuration of FIG. 1C, the size of the total scattered light signal is twice as large as the scattered light signal of FIG. 1A. Also, in FIG. 1C, the background scattered light is generated from two illumination spots equivalent to FIG. 1A. Since each photodetector can detect only the background scattered light from one illumination spot, however, the background scattered light strength detected by each photodetector is equal to that of FIG. 1A. For the same reason as described in FIG. 1B, in the case where the scattered signals from the two photodetectors 7, 8 are added, the size of the noise contained in the sum is $\sqrt{2}$ times as large as in FIG. 1A. As a result, the relative value of S/N of FIG. 1C with S/N of FIG. 1A as unity is $\sqrt{2}$, both the total scattered light signal and the noise being twice as large. As compared with FIG. 1A, therefore, S/N is improved $\sqrt{2}$ times. It is easily understood that S/N can be improved $\sqrt{N}$ times in the case where the configuration shown in FIG. 1C is assumed to involve not 2 but N illumination spots and N photodetectors as a general case.

In the configuration of FIGS. 1A to 1C, the inspection speed is equal, and therefore, it is understood from the foregoing description that the detection sensitivity of the contaminant particle or defect can be improved without sacrificing the time required for inspection of the whole surface of the sample by the configuration in which a plurality of illumination spots are juxtaposed not to be superposed one on another along the direction of primary scanning of the sample stage and the scattered light signal from each of the plurality of the illumination spots is isolated and detected. Also, it has been found that this configuration can be realized by detecting the scattered light with the photodetectors corresponding to the plurality of illumination spots, respectively.

Nevertheless, it is not easy to detect the scattered light by individual photo detectors corresponding to the plurality of the illumination spots, respectively, by reason of the facts that:

(1) In order to make sure that only the scattered light from a corresponding illumination spot enters each photodetector and no scattered light from the other illumination spots enters, a high-performance isolation imaging optics is required capable of imaging the images of the respective illumination spots at sufficient distance from each other not to be superposed one on another.

(2) Especially in the case where it is desired to detect the scattered light at a low elevation angle, the isolation imaging optics constitutes an oblique observation optics at low elevation angle, and therefore, the plurality of the illumination spots are distributed at spatial intervals substantially along the direction of focal depth of the optics, thereby making it difficult to realize the optics capable of imaging the illumination spots sufficiently isolated from each other.

(3) The provision of a plurality of combinations of the isolation imaging optic described in (1) and the photodetector including a photomultiplier tube high in detection sensitivity corresponding to a plurality of illumination spots requires a large mounting volume. Especially, in the case where the scattered light is detected at each position of a plurality of elevation angles and a plurality of azimuthal angles combined, a plurality of combinations of the isolation imaging optics described in (1) and the photomultiplier tube high in detection sensitivity corresponding to the plurality of the illumination spots are required at respective positions of scattered light detection, resulting in a very large mounting volume. As a result, the parts, interfering with each other spatially, may be impossible to arrange. A solution may be to use small photodetectors or photodetectors each having a plurality of pixels. Regrettably, however, this type of photodetector having a sufficiently high detection sensitivity as compared with the photomultiplier tube is not available and impossible to employ.

In order to obviate the aforementioned disadvantage and provide an easy-to-realize method of improving the detection sensitivity, this invention provides a technique for isolating and detecting the scattered light from a plurality of illumination spots using a single but not a plurality of photodetectors.

Figure 3:
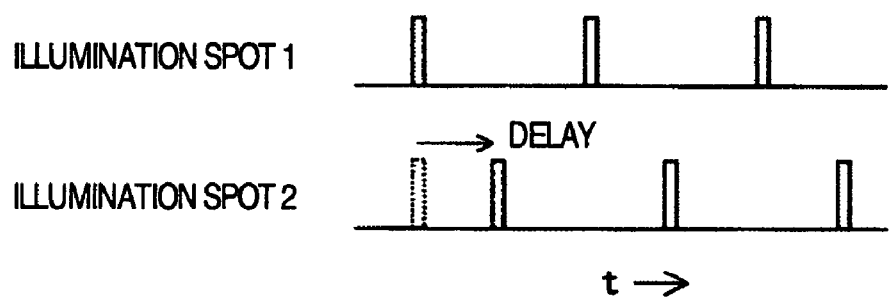
FIG. 3 is a diagram showing the light emission timing of a plurality of illumination spots.

This technique is explained in detail with reference to FIG. 3. An illumination beam source 11 is constituted of a pulse laser for generating pulses by temporally repetitive pulse oscillation. The pulses are generated at such time intervals that the light is emitted a plurality of times during the time when a contaminant particle 1 passes through an illumination spot by primary scanning. The light emitted from the light source 11 is split into two beams 21, 22 by a beam splitter 12. The beams 21, 22 both finally enter a radiation lens 18 and form illumination spots 3, 4, respectively. Optical paths are formed in such a manner that the beam 22 passes along a longer optical path than the beam 21 in the meantime. In the case where the pulse oscillation interval of the pulse laser source 11 is 10 ns, for example, the delay time can be set to just one half of the time of the pulse oscillation interval by setting the difference in optical path length to 1500 mm, as indicated by the following equation:

Distance covered by light for 5 ns=$(3\times10^{11})\times(5\times10^{-9})$ (mm)=1500 (mm)

The optical paths of the beams 21, 22 include beam splitters 14, 15 for retrieving a part of the beams 21, 22 as a light emission timing signal generating means to retrieve the light emission timing of each laser light as a signal, and photodiodes 16, 17 for converting the time change signal waveform of the partly retrieved light into an electrical signal. In order to correctly detect the light emission time difference between the two illumination spots 3, 4, the two photodiodes 16, 17 are of course required to be arranged equidistantly in the reverse way of the optical paths of the beams 21, 22 from the illumination spots. The light emission timing signal obtained from the photodiodes 16, 17 has the waveform, for example, as shown in the two upper stages of FIG. 4.

Figure 4:
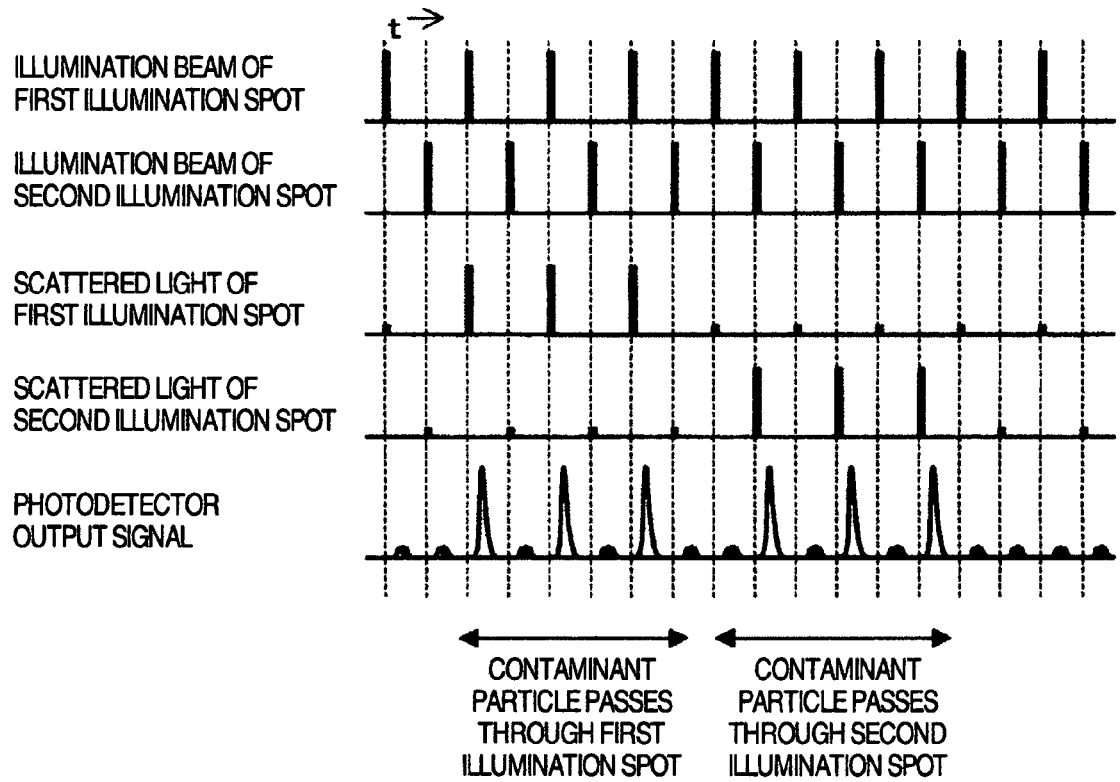
FIG. 4 is a diagram showing the light emission timing of the scattered light from each illumination spot.

Like in the configuration of FIG. 1B, the contaminant particle 1, after passing through the first illumination spot 3, passes through the second illumination spot 4, so that the scattered light signal is obtained twice from the photodetector 7. The light source 11 is a pulse laser. As long as the time response speed of the photodetector 7 is sufficiently high (this assumption is sufficiently realistic for the photomultiplier tube), therefore, the temporal strength change of the scattered light signal generated while passing through each illumination spot assumes not a continuous waveform but, as shown in FIG. 4, a discrete waveform corresponding to the pulse oscillation of the light source 11. As understood from FIG. 4, the illumination beam is radiated not strictly at the same time on the first illumination spot 3 and the second illumination spot 3, and therefore, the second scattered light from the first illumination spot 3 and the scattered light from the illumination spot 4 are not generated at the same time point. According to this invention, the actual time point when the illumination beam is radiated on each illumination spot can be accurately determined by the light emission timing signal generating means described above. By isolating the output signal of the photodetector 7 using this light emission timing signal, therefore, the scattered light signals from a plurality of illumination spots can be isolated and detected using a single photodetector. An example of the circuit configuration for this operation is shown in FIG. 5.

The output signal of the photodetector 7, after being amplified by a preamplifier 25, is distributed to two gate circuits 27. The on/off operation of each gate circuit is controlled in accordance with the light emission timing signals from the photodiodes 16, 17. Generally, however, as shown in the fifth stage of FIG. 6, the output signal of the photodetector rises behind the light emission timing of the illumination beam and the frequency response speed is low as compared with the light emission duration (for example, about 15 ps) of the pulse laser. Therefore, the pulse width of the output signal of the photodetector is longer than the light emission duration of the illumination beam. In view of this, the light emission timing signals from the photodiodes 16, 17 are given a predetermined delay time and a predetermined pulse duration by a waveform shaper 28. The output signal from the waveform shaper 28 assumes, for example, the waveforms shown in the third and fourth stages of FIG. 6. The gate circuits 27 are turned on/off by the gate signal from this waveform shaper 28, so that the isolated scattered light signals corresponding to each illumination spot shown in the sixth and seventh stages of FIG. 6 are generated from the output signal of the preamplifier 25. Each scattered light signal thus isolated is thereafter amplified further by the amplifiers 26. It is thus understood that the use of the circuit shown in FIG. 5 makes it possible to detect by isolating the scattered light signal corresponding to a plurality of illumination spots, and each scattered light signal thus isolated is not affected by the background light of the illumination spot other than the corresponding one.

In the aforementioned case, the signal is isolated using the gate circuits 27. A similar advantage is achieved, however, by a configuration shown in FIG. 7, in which integrators 29 are arranged in place of the gate circuits 27, and the integrating operation of the integrators 29 is controlled by the signal of the waveform shaper 28.

Figure 2:
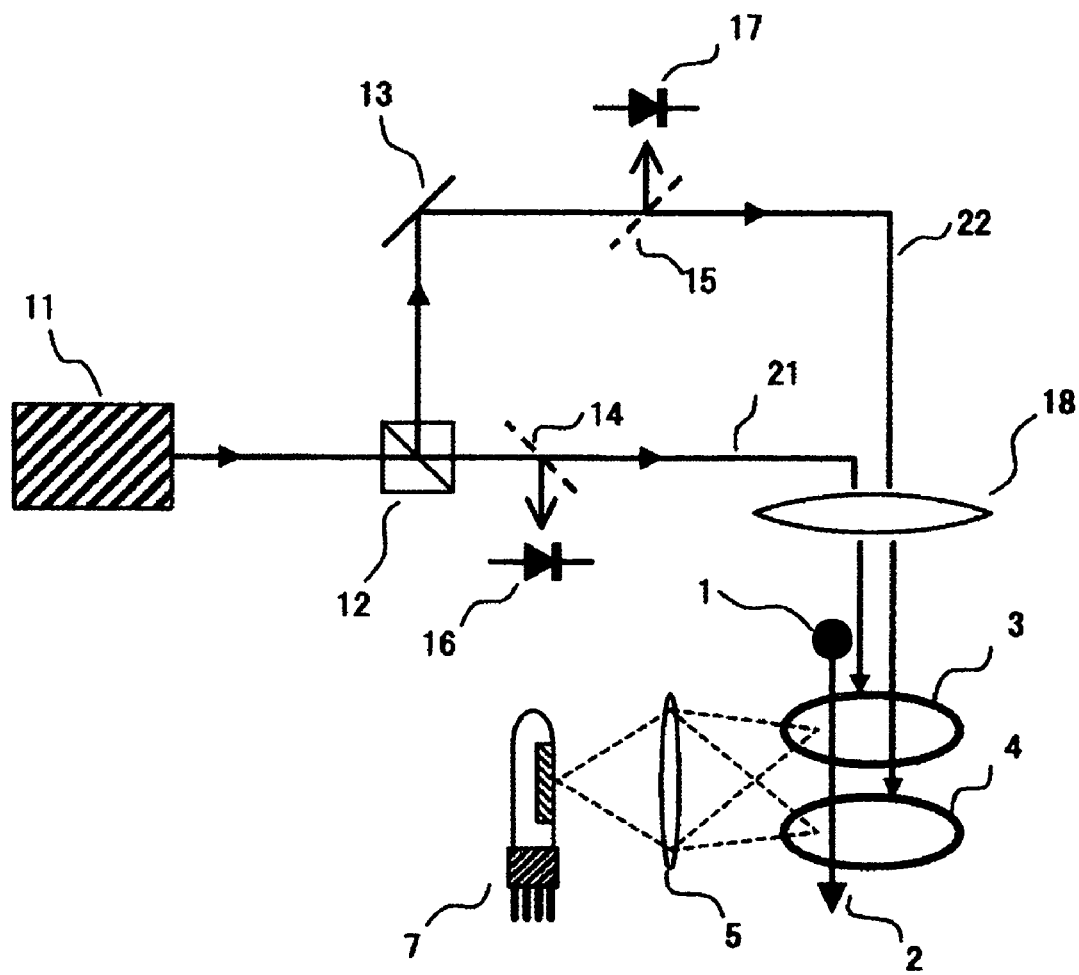
FIG. 2 is a diagram for explaining the technique for improving the detection sensitivity of contaminant particles or defects without sacrificing the time required for inspection of the whole surface of a sample according to this invention.
Figure 5:
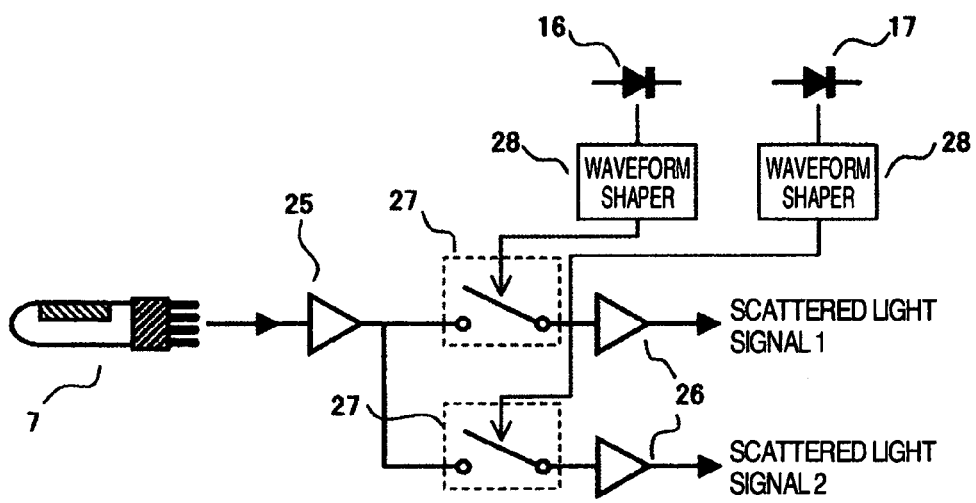
FIG. 5 shows a circuit for isolating the signal using a plurality of gate circuits.
Figure 6:
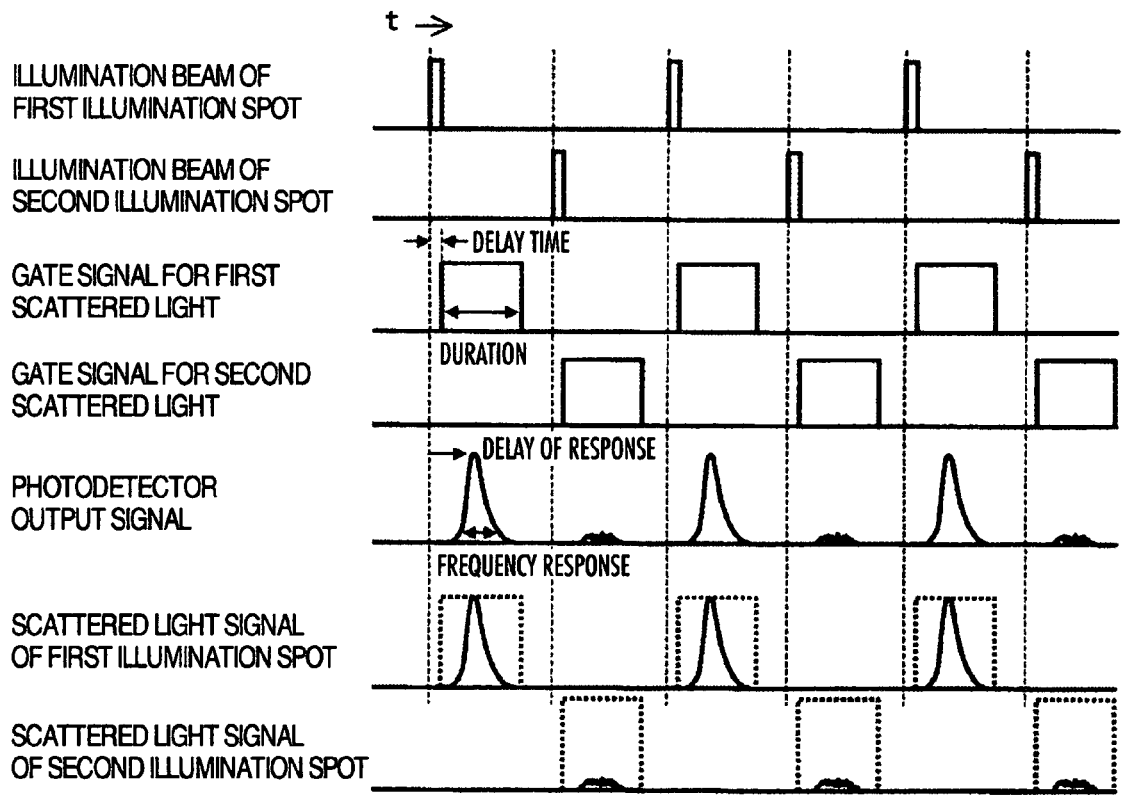
FIG. 6 is a diagram for explaining the gate signal generated from the light emission start timing signal.
Figure 7:
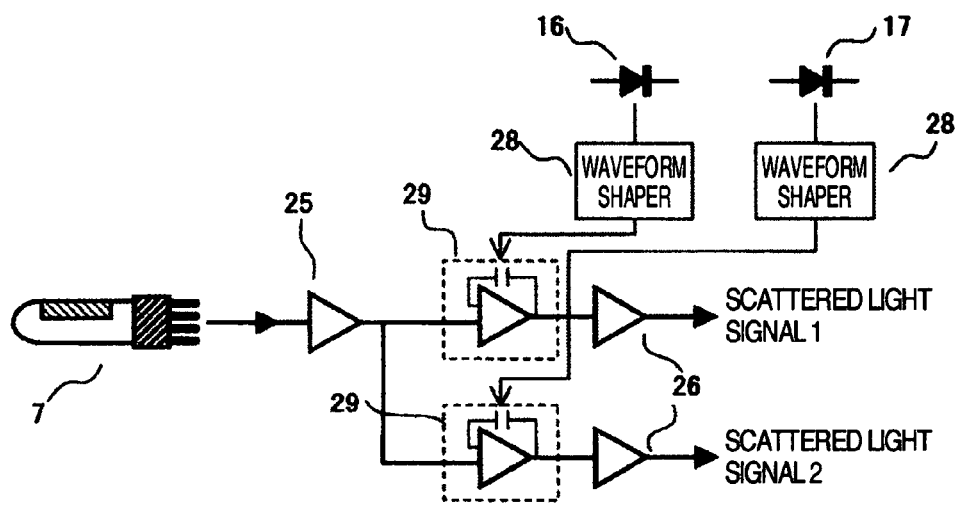
FIG. 7 shows a circuit for isolating the signal using a plurality of integrators.

In a combined configuration of the optics shown in FIG. 2 and the circuit shown in FIG. 5 or 7, assuming that sum of the two scattered light signals is calculated as the total scattered light signal, the size of the total scattered light signal is twice as large as the scattered light signal for the configuration shown in FIG. 1A. Also, each scattered light signal isolated by the circuit of FIG. 5 or 7 is affected by the background scattered light from only one illumination spot, and therefore, the noise contained in each scattered light signal is equal to the case of the configuration of FIG. 1A, and the size of the noise contained in the sum of the two scattered light signal is $\sqrt{2}$ times as large as in FIG. 1A. As a result, in view of the fact that the total scattered light signal is twice and the noise $\sqrt{2}$ times as large, the value of S/N of the configuration shown in FIGS. 3 and 5 relative to S/N of FIG. 1A as unity is improved $\sqrt{2}$ times as large. This is as effective as when the two photo-detectors are used as shown in FIG. 1C. Although the configuration of FIGS. 2, 5, 7 is explained with two illumination spots, it will be easily understood that S/N can be improved $\sqrt{N}$ times in a generalized case where the number of illuminations is N instead of 2. In the aforementioned case where N is 2, the final result is determined as a simple sum. In the case where N is larger than 2, on the other hand, the final scattered light signal may be obtained by more complicated statistical process. Also, in spite of the foregoing explanation that the light emitted when the contaminant particle 1 passes through the illumination spot is assumed to be the scattered light, this light may be generalized as the scattered/diffracted/reflected light. Further, instead of the contaminant particle existing on the surface of a sample, the invention is equally applicable to defects such as a scratch or a crystal defect other than the contaminant particle existing in the neighborhood of as well as on the surface of the sample.

As described above, the optical inspection apparatus includes a pulse laser source for oscillating the temporally repetitive pulses, wherein one light flux emitted from the pulse laser source is split into a plurality of light fluxes, after which a different delay time is given to each light flux. These light fluxes are radiated at a plurality of positions substantially aligned at predetermined spatial intervals in a manner not to be superposed one on another substantially along the same direction as primary scanning of the sample stage thereby to form a plurality of illumination spots on the surface of the sample. The photo detector to which the scattered/diffracted/reflected light generated from the plurality of the illumination spots are adapted to enter substantially at the same time detects the particular scattered/diffracted/reflected light. The output signal from the photodetector is controlled based on the light emission start timing signal from the light emission start timing signal generating means indicating the light emission start timing of each of the plurality of light fluxes given mutually different delay time. In this way, the scattered/diffracted/reflected light signal due to the scattered/diffracted/reflected light from each of the plurality of illumination spots is isolated and detected. With this configuration, the detection S/N is improved for an improved detection sensitivity of the contaminant particle or defect without sacrificing the time required for inspection of the whole surface of the sample.

Although the foregoing description of the prior art deals with a technique for detecting the scattered/diffracted/reflected light from a plurality of directions with a plurality of elevation angles and a plurality of azimuthal angles combined, the technique according to the invention described above is applicable also to the detection method for each of a plurality of directions with a plurality of the elevation angles and a plurality of azimuthal angles combined. The direction in which the illumination beam is incident on the sample surface may of course be either oblique or normal.

Figure 8:
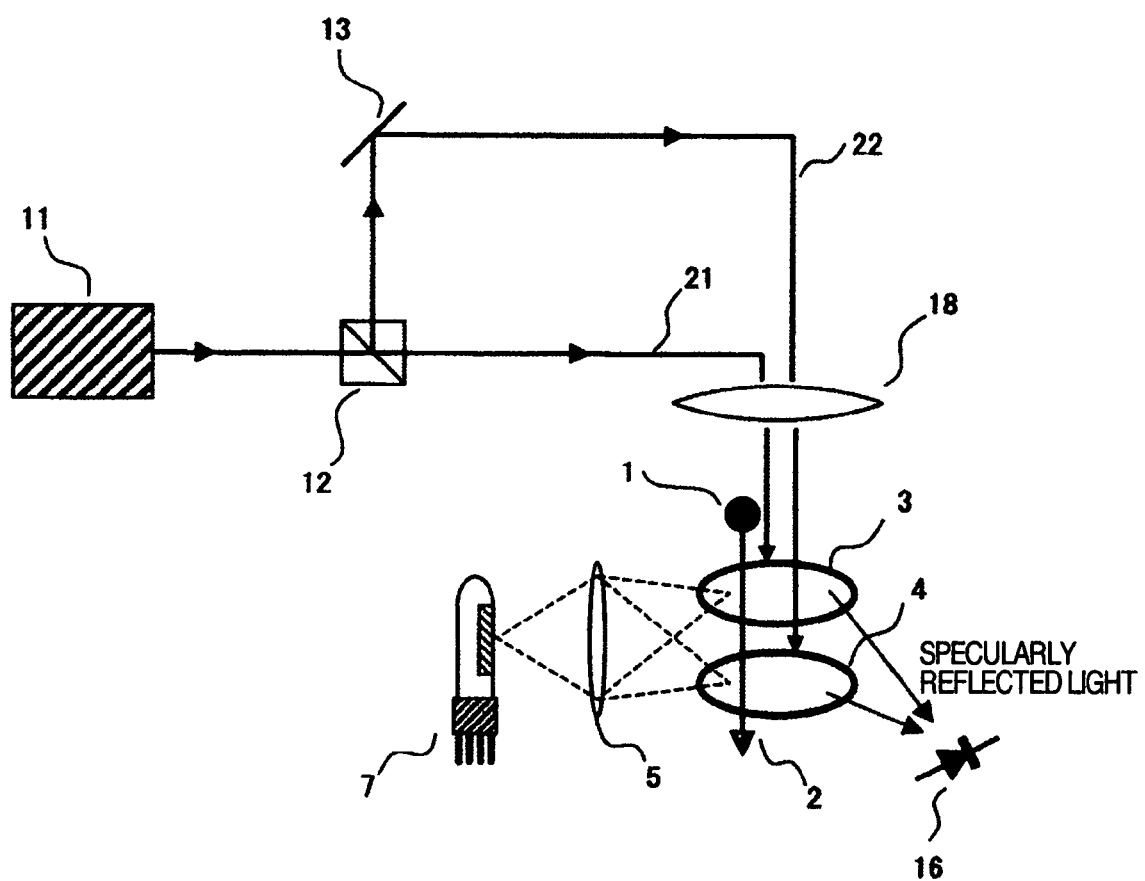
FIG. 8 is a diagram for explaining another light emission timing signal generating means.

In the circuit shown in FIG. 5 or 7, the signal is isolated by use of the light emission timing signal from the light emission timing signal generating means shown in FIG. 2. In the optics shown in FIG. 2, this light emission timing is optically monitored on two optical paths of radiated beams. As shown in FIG. 8, however, a part of the light specularly reflected from the two illumination spots may alternatively be optically monitored. Also, as described above, the signal of the photodetector is lower in frequency response speed, and therefore, only the light emission start timing information of the aforementioned timing signal is required, and the means used for the detection gate function as described in JP-A-2000-338048 which faithfully grasps the emitted light waveform of the actual pulse laser is not required. This light emission timing signal, therefore, may be replaced by a light emission start timing signal capable of faithfully reproducing only the information on the light emission start timing of each light emission pulse. Further, the use of the light emission start timing alone eliminates the need of optically monitoring the actual light emission of the laser beam as in FIGS. 2 and 8, and the light emission start timing signal may be generated based on the light emission sync signal output from the pulse laser 11 or the light emission control signal applied to the pulse laser 11 from an external source to control the pulse laser 11. In such a case, the delay time of the second illumination spot having the light emission timing behind the first illumination spot can be determined in advance by calculating the difference between the two optical path lengths.

Figure 9:
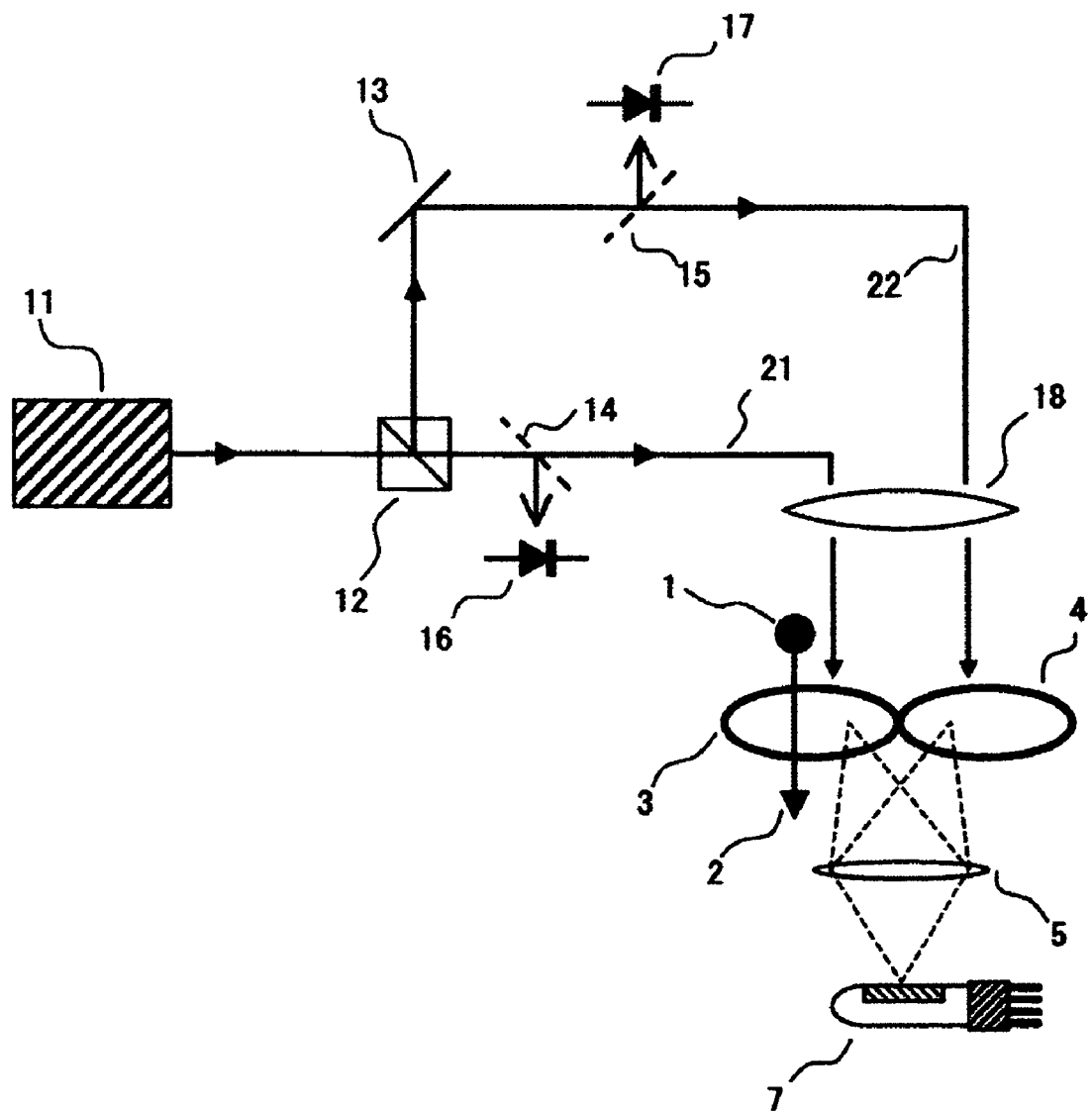
FIG. 9 is a diagram for explaining a first technique for improving the time required for inspection of the whole surface of the sample without sacrificing the detection sensitivity of contaminant particles or defects according to the invention.

Next, the technique according to the invention in which the time required for inspecting the whole surface of the sample is improved without sacrificing the detection sensitivity of a contaminant particle or a defect is explained with reference to FIG. 9. The configuration of FIG. 9 is different from that of FIG. 2 only in the spatial allocation of two illumination spots, and the operation, being identical, is not explained in detail. In the configuration of FIG. 2, the two illumination spots are substantially aligned substantially along the same direction as the primary scanning of the sample stage at predetermined spatial intervals with each other in a manner not to be superposed one on the other. In FIG. 9, on the other hand, the two illumination spots are substantially aligned closely in a manner not to be superposed one on the other in substantially the same direction as the secondary scanning of the sample stage. In this configuration, the scattered light signals corresponding to the illumination spots 3, 4 can be isolated and detected from the output signal of the photodetector 7 by exactly the same function as explained in the configuration of FIG. 2. It is understood that each of these scattered light signals, in both the scattered light strength and the noise level contained, is equal to the configuration shown in FIG. 1A. As a result, with this configuration, the width of the two illumination spots along the direction of secondary scanning is twice as large as in FIG. 1B. With a detection sensitivity equal to FIG. 1A, therefore, the inspection speed can be improved to twice as high. Although the configuration of FIG. 9 is explained on the assumption of two illumination spots, it will be easily understood that the inspection speed is improved to N times as high in the case where the number of illumination spots is not 2 but N as a general case.

As described above, the optical inspection apparatus according to this embodiment, having a pulse laser source for oscillating temporally repetitive pulses, is so configured that one light flux emitted from the pulse laser source is splitted into a plurality of light fluxes, after which each light flux is given a different delay time, and a plurality of illumination spots are formed by radiating the light at a plurality of positions substantially aligned closely in a manner not to be superposed one on another in substantially the same direction as the secondary scanning of the sample stage. Then, a photo detector entered substantially at the same time by the scattered/diffracted/reflected light generated from the plurality of the illumination spots detects the scattered/diffracted/reflected light, and the output signal of the photodetector is controlled based on the light emission start timing signal from the light emission start timing signal generating means arranged inside or outside the illumination means for indicating the light emission start timing of each of a plurality of light fluxes given different delay time. In this way, the scattered/diffracted/reflected light signal due to the scattered/diffracted/reflected light from the plurality of the illumination spots are isolated and detected. Thus, without sacrificing the detection sensitivity, the time required for inspecting the whole surface of the sample can be improved.

Although the conventional technique described above represents a case in which the scattered/diffracted/reflected light is detected from a plurality of directions with a plurality of elevation angles and a plurality of azimuthal angles combined, the aforementioned technique according to the invention is applicable to a method of detection in each of a plurality of directions with the plurality of elevation angles and the plurality of azimuthal angles combined. The direction in which the illumination beam is incident to the sample surface may of course be either oblique or normal.

Figure 10A:
FIGS. 10A, 10B are diagrams for explaining a method of arranging a plurality of illumination spots.
Figure 10B:
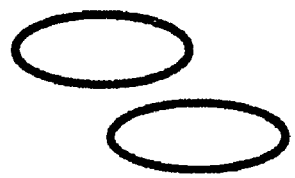
Figure 11:
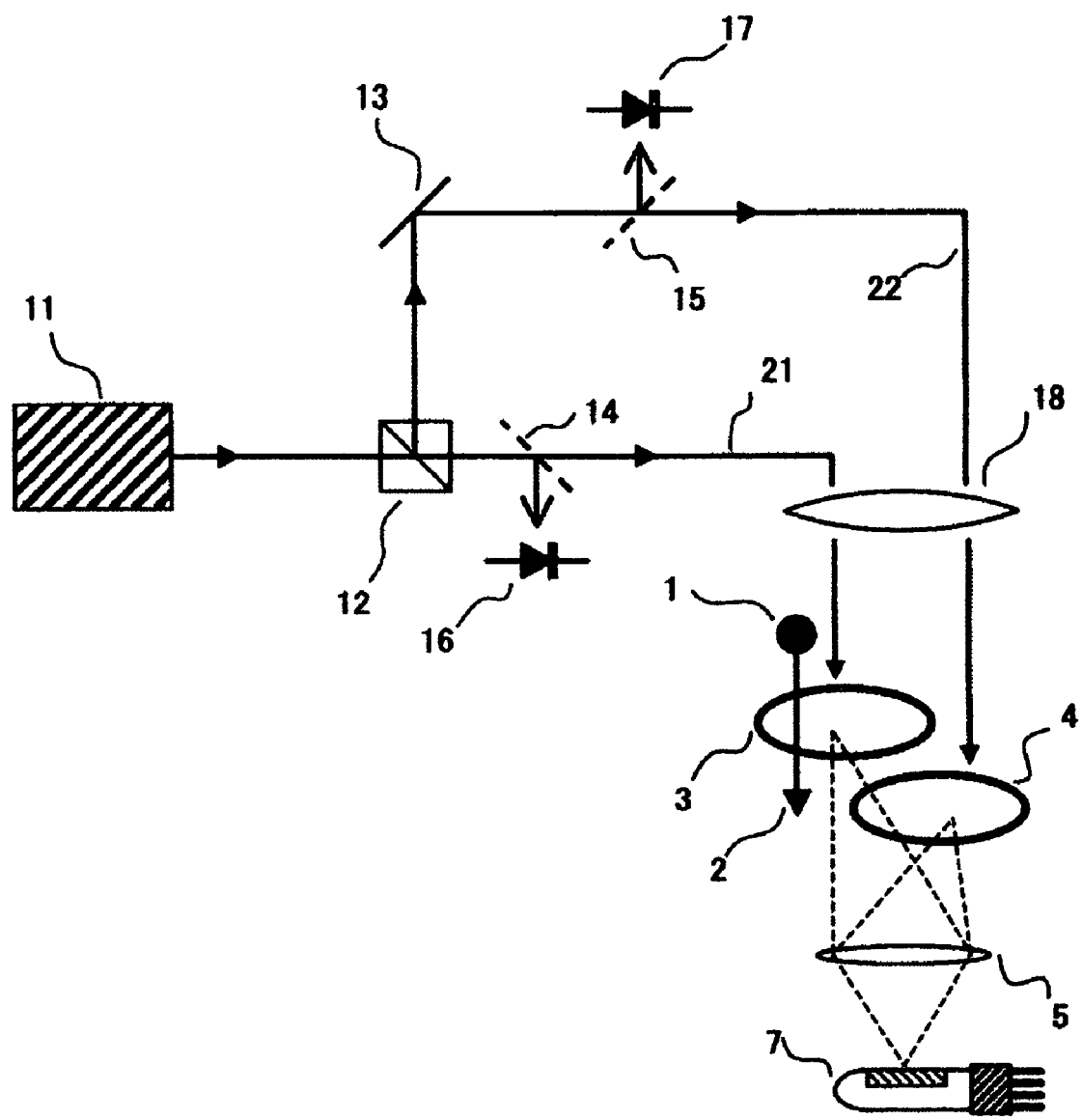
FIG. 11 is a diagram for explaining a second technique for improving the time required for inspection of the whole surface of the sample without sacrificing the detection sensitivity of contaminant particles or defects according to the invention.

In the case described above, a plurality of illumination spots are substantially aligned closely not in superposition with each other in substantially the same direction as the secondary scanning of the sample stage. In the case where it is not desired to use the outer edge of each illumination spot low in illuminance or to improve the detection accuracy by detecting each contaminant particle by two primary scans, then, as shown in FIG. 10A, a plurality of illumination spots are suitably superposed one on another at a predetermined ratio. In the superposed area of the illumination spots, however, the energy of the illumination beams of the two illumination spots is received, and therefore, temperature increases to such an extent that the sample may be thermally damaged considerably. In view of this, the plurality of illumination spots are arranged displaced at predetermined intervals in the direction of primary scanning as shown in FIG. 10B. Thus, while the superposition of illumination spots is obviated, the effect of thermal damage is avoided. At the same time, the loci plotted by the illumination spots by primary scanning are superposed one on another at a predetermined ratio, and therefore, the original object described above can be achieved. In other words, this arrangement is equivalent to the arrangement of illumination spots substantially in alignment along a predetermined direction at an angle to the direction of primary scanning of the sample stage between the translation direction and the orthogonal direction. The configuration in which a part of the plurality of illumination spots shown in FIG. 9 is changed partially into the arrangement of illumination spots as shown in FIG. 10B is shown in FIG. 11. The advantage obtained by this configuration other than that obtained from the superposition of the illumination spots is identical with that shown in FIG. 9, and therefore not described again.

Figure 12:
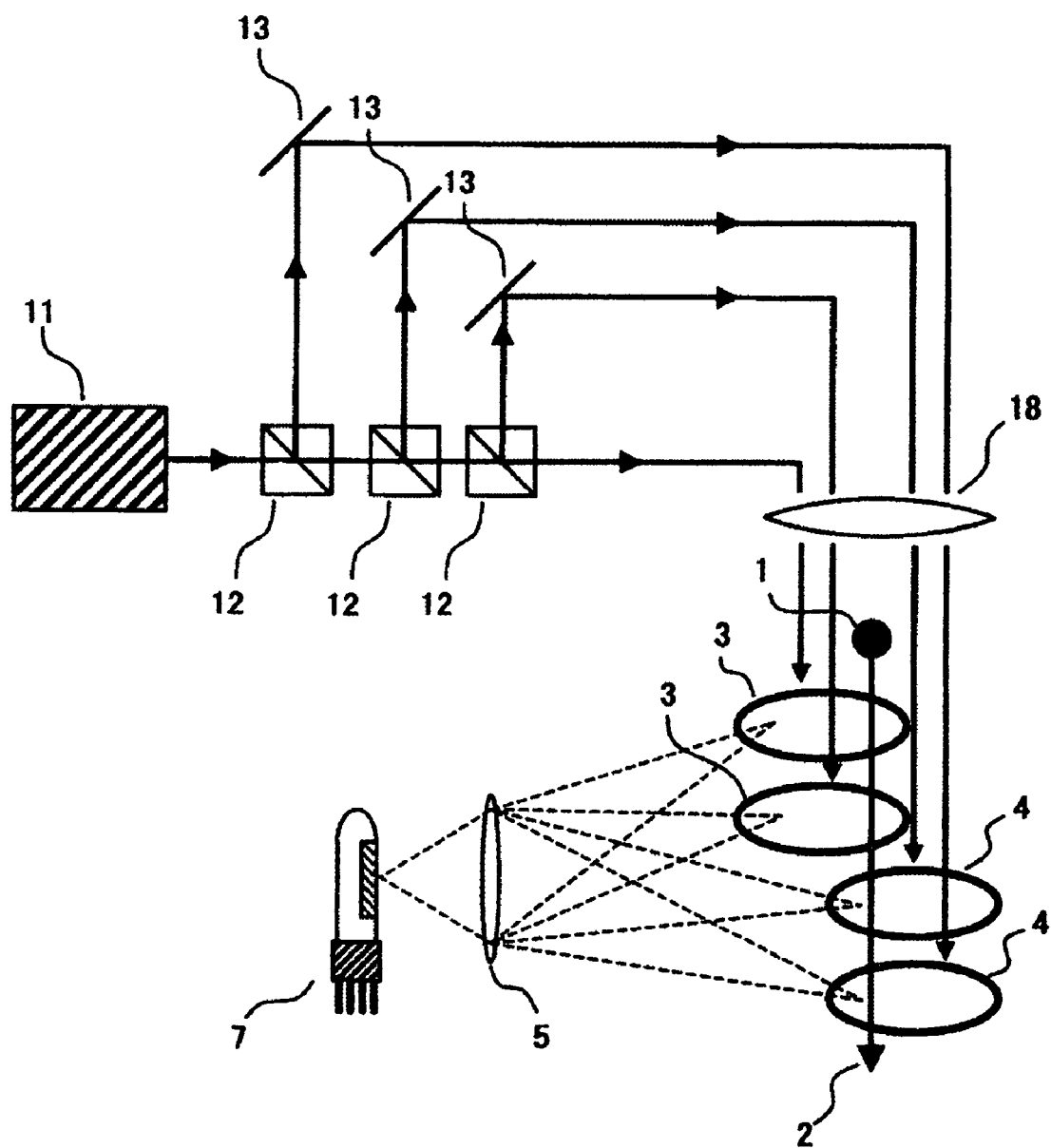
FIG. 12 is a diagram for explaining a technique to improve both the detection sensitivity of contaminant particles or defects and the time required for inspection of the whole surface of a sample at the same time according to this invention.

Further, the arrangement of illumination spots shown in FIG. 2 may be combined with that shown in FIG. 11. Specifically, assuming that M and N are integers, a plurality of illumination spots in the number of M×N are divided into N groups of M illumination spots, the M illumination spots in each of the N groups are substantially aligned in substantially the same direction as the primary scanning of the sample stage on the sample surface. At the same time, the N groups each including M illumination spots are substantially aligned in a predetermined direction at an angle to the primary scanning of the sample stage between the translation direction and the orthogonal direction. An example of this configuration with M=2 and N=2 is shown in FIG. 12. The beam splitter and the photodiode making up the light emission start timing generating means, though not described, are arranged at positions equidistantly located along the reverse optical path from each illumination spot in each optical path of the four radiation beams shown in FIG. 12.

As will be readily understood, this configuration can produce the advantages of the configurations of both FIG. 2 and FIG. 11. Specifically, the detection sensitivity of the contaminant particle or defect and the time required for inspecting the whole surface of the sample are improved at the same time.

Although FIG. 12 employs the method of arrangement in the configuration of FIG. 11 to arrange the illumination spots in the direction of secondary scanning, the illumination spots may alternatively be arranged closely in the direction of secondary scanning as shown in the configuration of FIG. 9.

Figure 13:
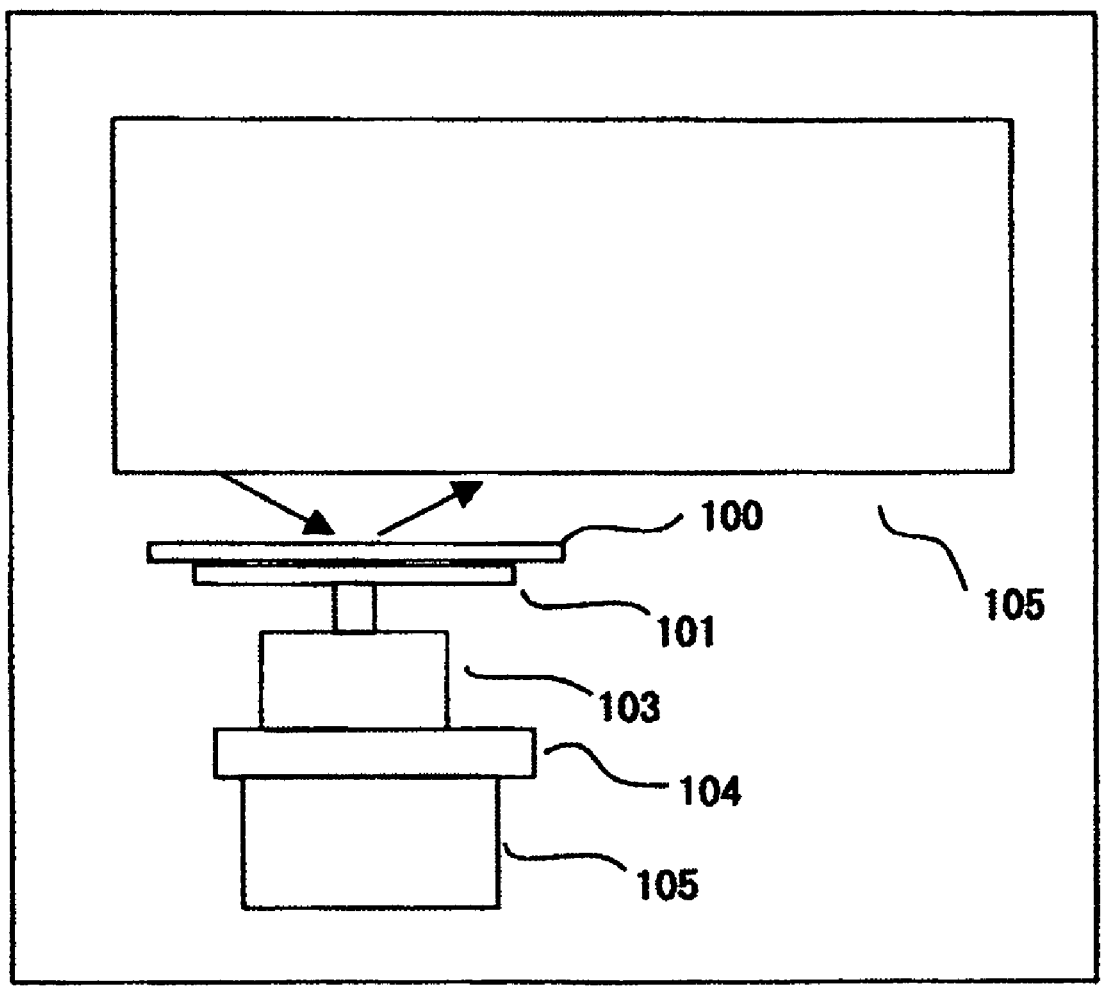
FIG. 13 is a diagram showing a configuration of a contaminant particle/defect inspection apparatus according to an embodiment of the invention.

A contaminant particle/defect inspection apparatus using the contaminant particle/defect detection method according to an embodiment of this invention is shown in FIG. 13. A semiconductor wafer 100 making up a sample to be inspected is attached by vacuum to a chuck 101, which in turn is mounted on a sample stage 102 including a rotation stage 103, a translation stage 104 and a Z stage 105. An illumination/detection optics 110 arranged above the semiconductor wafer 100 is the optical system shown in FIG. 11. Specifically, the light source 11 of the illumination beam is comprised of a pulse laser for oscillating pulses temporally repetitively. The pulses are oscillated at such time intervals that light is emitted a plurality of times within the time while the contaminant particle 1 passes through the illumination spot by primary scanning. The light emitted from the light source 11 is split into two beams 21, 22 by a beam splitter 12. The beams 21, 22 both enter a radiation lens 18 finally to form the illumination spots 3, 4, respectively. In the process, however, the optical paths are so configured that the delay time of the beam 22 behind the beam 21 corresponds to just one half of the time of the pulse oscillation interval. The optical paths of the beams 21, 22 each have arranged thereon beam splitters 14, 15 for retrieving a part of the beams 21, 22 as a light emission start timing generating means for retrieving the light emission start timing of each laser beam as a signal and photodiodes 16, 17 for converting the temporal change waveform of the light partly retrieved by the beam splitters 14, 15 into an electrical signal. In order to correctly detect the light emission time difference between the two illumination spots 3, 4, the two photodiodes 16, 17 are arranged equidistantly in reverse way of the optical path of the beams 21, 22 from the illumination spot side. Each illumination beam is irradiated onto the surface of the semiconductor wafer 100 in oblique incidence substantially with Brewster angle of crystal Si. Also, the condenser lens 5 is configured to focus the scattered light at a low elevation angle to capture the scattered light efficiently for fine contaminated particles subjected to Rayleigh scattering. In this configuration, the contaminated particle 1, after passing through the first illumination spot 3, passes through the second illumination spot 4, so that the scattered light signal is produced twice from the photodetector 7. The output signal of the photodetector 7 is processed by a circuit configured as shown in FIG. 7. Specifically, the output signal of the photodetector 7, after being amplified by a preamplifier 25, is distributed to two integrators 29. The integrating operation of each integrator is turned on/off by the integration control signal produced by giving a predetermined delay time and a predetermined pulse duration to the light emission start timing signal from the photodiodes 16, 17 through a waveform shaper 28, thereby isolating the scattered light signal corresponding to each illumination spot. Each scattered light signal thus isolated is further amplified by an amplifier 26. By use of the circuit of FIG. 7 in this way, the scattered light signals corresponding to a plurality of illumination spots can be isolated and detected from the output of a single photodetector 7. Each scattered light signal thus isolated is not affected by the background light of the illumination spots other than the corresponding ones. As a result, the contaminated particle/defect inspection apparatus according to an embodiment of the invention shown in FIG. 13 can improve the time required for inspection of the whole surface of the sample without sacrificing the detection sensitivity.

Instead of two illumination spots employed in the configuration of FIG. 13, illumination spots in the number of N not less than 2 can be used, in which case the inspection speed is improved N times.

Although the embodiment of the invention described above has only one direction in which the scattered light is detected, the scattered light may alternatively be detected from a plurality of directions by arranging the aforementioned detection system in each of a plurality of directions with a plurality of elevation angles and a plurality of azimuthal angles combined. The illumination beam may of course be radiated on the sample surface either obliquely or normally.

Also, in spite of the method of arranging a plurality of illumination spots shown in FIG. 11, the arrangement shown in any of FIGS. 2, 9, 12 may of course alternatively be used.

It should be further understood by those skilled in the art that although the foregoing description has been made on embodiments of the invention, the invention is not limited thereto and various changes and modifications may be made without departing from the spirit of the invention and the scope of the appended claims.

The invention claimed is:

1. An optical inspection method for detecting a contaminant particle/defect existing on a surface or in an internal part near a surface of a sample, using a sample stage adapted for first translation movement in primary scanning and second translation movement along a direction substantially orthogonal to the first translation movement in secondary scanning or a sample stage adapted for rotational movement in primary scanning and translation movement in secondary scanning, a pulse laser source for oscillating pulses temporally repetitively, an illumination unit for radiating a pulse light from a light source on the surface of the sample, and a scattered/diffracted/reflected light detection unit for detecting the radiated light scattered/diffracted/reflected on the sample, wherein the illumination unit includes a unit for splitting a single light flux emitted from the pulse laser source into a plurality of light fluxes, a time delay optics for giving a different delay time for each of the plurality of the split light fluxes, a unit for forming a plurality of illumination spots by radiating the plurality of the light fluxes having different delay time at a plurality of discrete positions in predetermined spaced relationship to each other on the surface of the sample, and a light emission timing signal generating unit for indicating the light emission timing of each of the plurality of the light fluxes having different delay time inside or outside the illumination unit, and wherein the scattered/diffracted/reflected light detection unit includes a photodetector substantially simultaneously entered by the scattered/diffracted/reflected light generated from the plurality of the illumination spots on the surface of the sample, and the scattered/diffracted/reflected light signal due to the scattered/diffracted/reflected light from each of the plurality of the illumination spots is isolated and detected by controlling the output signal of the photodetector based on the light emission timing signal.

2. An optical inspection method used with an optical inspection apparatus for detecting a contaminant particle/defect existing on a surface or in an internal part near a surface of a sample to be inspected, comprising selected one of a sample stage adapted for first translation movement in primary scanning and second translation movement along a direction substantially orthogonal to the first translation movement in secondary scanning and a sample stage adapted for rotational movement in primary scanning and translation movement in secondary scanning, a pulse laser source for oscillating pulses temporally repetitively, an illumination unit for radiating the pulse light from a light source on the surface of the sample, and a plurality of scattered/diffracted/reflected light detection units or detecting the radiated light scattered/diffracted/reflected on the sample in selected one of a plurality of elevation angles and a plurality of azimuthal angles and a combination of the plurality of elevation angles and the plurality of azimuthal angles with respect to the surface of the sample, wherein the illumination unit includes a unit for splitting a single light flux emitted from the pulse laser source into a plurality light fluxes, a time delay optics for giving a different delay time for each of the plurality of light fluxes splitted, and a unit for forming a plurality of illumination spots by radiating the plurality of the light fluxes having different delay time at a plurality of discrete positions in predetermined spaced relationship to each other on the surface of the sample, and a light emission timing signal generating unit for indicating the light emission timing of each of the plurality of the light fluxes having different delay time inside or outside the illumination unit, and wherein each of the plurality of the scattered/diffracted/reflected light detection units includes a photodetector substantially simultaneously entered by the scattered/diffracted/reflected light generated from the plurality of the illumination spots on the surface of the sample, and the scattered/diffracted/reflected light signal due to the scattered/diffracted/reflected light from each of the plurality of the illumination spots is isolated and detected by controlling the output signal from the photodetector based on the light emission timing signal.

3. The optical inspection method according to claim 1, wherein the light emission timing signal generating unit generates a light emission timing signal based on selected one of a sync signal output from the pulse laser source and a control signal applied to the pulse laser source.

4. The optical inspection method according to claim 1, wherein the light emission timing signal generating unit includes a light emission timing signal detection unit for isolating part of the plurality of light fluxes given different delay time, on the optical path before radiating the plurality of light fluxes onto the sample surface, thereby to detect the light emission timing of each light flux.

5. The optical inspection method according to claim 1, wherein a specularly reflected light detection unit detects the radiated light specularly reflected on the sample, and the light emission timing signal generating unit generates a light emission timing signal based on the specularly reflected light detection signal detected by the specularly reflected light detection unit.

6. An optical inspection method used with an optical inspection apparatus for detecting a contaminant particle/defect existing on a surface or in an internal part near a surface of a sample to be inspected, comprising a sample stage adapted for selected one of a combination of first translation movement in primary scanning and second translation movement in a direction substantially orthogonal to the first translation in secondary scanning and a combination of rotational movement in primary scanning and translation movement in secondary scanning, a pulse laser source adapted for temporally repetitive pulse oscillation, an illumination unit for radiating the pulse light from a light source on the surface of the sample and a scattered/diffracted/reflected light detection unit for detecting the radiated light scattered/diffracted/reflected on the sample surface, wherein the illumination unit includes a unit for splitting a single light flux emitted from the pulse laser source into a plurality light fluxes, a time delay optics for giving a different delay time for each of the plurality of light fluxes splitted, a unit for forming a plurality of illumination spots by radiating the plurality of the light fluxes having different delay time at a plurality of discrete positions in predetermined spaced relationship to each other on the surface of the sample, and a light emission start timing signal generating unit for indicating the light emission start timing of each of the plurality of the light fluxes having different delay time inside or outside the illumination unit, and wherein the scattered/diffracted/reflected light detection unit includes a photodetector substantially simultaneously entered by the scattered/diffracted/reflected light generated from the plurality of the illumination spots on the surface of the sample, and the scattered/diffracted/reflected light signal due to scattered/diffracted/reflected light from each of the plurality of the illumination spots is isolated and detected by controlling the output signal of the photodetector based on the light emission start timing signal.

7. An optical inspection method used with an optical inspection apparatus for detecting a contaminant particle/defect existing on a surface or in an internal part near a surface of a sample to be inspected, comprising selected one of a sample stage adapted for first translation movement in primary scanning and second translation movement along the direction substantially orthogonal to the direction of the first translation movement in secondary scanning and a sample stage adapted for rotational movement in primary scanning and translation movement in secondary scanning, a pulse laser source adapted for temporally repetitive pulse oscillation, an illumination unit for radiating the pulse light from a light source on the surface of the sample, and a plurality of scattered/diffracted/reflected light detection units for detecting the radiated light scattered/diffracted/reflected on the sample at selected one of a plurality of elevation angles and a plurality of azimuthal angles on the one hand and a plurality of combinations of a plurality of elevation angles and a plurality of azimuthal angles on the other hand, with respect to the surface of the sample, wherein the illumination unit includes a unit for splitting a single light flux emitted from the pulse laser source into a plurality of light fluxes, a time delay optics for giving a different delay time to each of the plurality of the split light fluxes, a unit for forming a plurality of illumination spots by radiating the plurality of the light fluxes having different delay time at a plurality of discrete positions in predetermined spaced relationship to each other on the surface of the sample, and a light emission start timing signal generating unit for indicating the light emission start timing of each of the plurality of the light fluxes having different delay time inside or outside the illumination unit, and wherein each of the plurality of the scattered/diffracted/reflected light detection units includes a photodetector substantially simultaneously entered by the scattered/diffracted/reflected light generated from the plurality of the illumination spots on the surface of the sample, and the scattered/diffracted/reflected light signal due to the scattered/diffracted/reflected light from each of the plurality of the illumination spots is isolated and detected by controlling the output signal from the photodetector based on the light emission start timing signal.

8. The optical inspection method according to claim 6, wherein the light emission start timing signal generating unit the light emission start timing signal based on selected one of the sync signal output from the pulse laser source and the control signal applied to the pulse laser source.

9. The optical inspection method according to claim 6, wherein the light emission start timing signal generating unit a light emission start timing signal detection unit for isolating a part of the plurality of light fluxes given different delay time on the light path before radiation of the plurality of light fluxes on the surface of the sample thereby to detect the light emission start timing of each of the light fluxes.

10. The optical inspection method according to claim 6, further comprising a specularly reflected light detection unit for detecting the radiated light specularly reflected on the sample, wherein the light emission start timing signal generating unit generates a light emission start timing signal based on the specularly reflected light detection signal detected by the specularly reflected light detection unit.

11. The optical inspection method according to claim 6, wherein the scattered/diffracted/reflected light signal due to the scattered/diffracted/reflected light from each of the plurality of illumination spots is isolated by controlling the output signal of the photodetector in such a manner that a light detection control signal, corresponding to each of the plurality of illumination spots, started at the light emission start timing and sustained for a predetermined time width is generated using the light emission start timing signal corresponding to each of the plurality of illumination spots, and the output signal from the photodetector is controlled based on the light detection control signal.

12. The optical inspection method according to claim 6, wherein the scattered/diffracted/reflected light signal due to the scattered/diffracted/reflected light from each of the plurality of illumination spots is isolated by controlling the output signal of the photodetector in such a manner that a light detection control signal, corresponding to each of the plurality of illumination spots, started a predetermined time behind each of the light emission start timing and sustained for another predetermined time width is generated using the light emission start timing signal corresponding to each of the plurality of illumination spots, and the output signal from the photodetector is controlled based on the light detection control signal.

13. The optical inspection method according to claim 6, wherein the scattered/diffracted/reflected light signal due to the scattered/diffracted/reflected light from each of the plurality of illumination spots is isolated by controlling the output signal of the photodetector in such a manner that a light detection control signal corresponding to each of the plurality of illumination spots is generated using the light emission start timing signal corresponding to each of the plurality of illumination spots, which light detection control signal is started behind each light emission start timing by the time corresponding to the rise time response characteristic of the output signal of the photodetector and sustained for a time width corresponding to the frequency band characteristic of the output signal of the photodetector, and wherein the output signal of the photodetector is controlled based on the light detection control signal.

14. The optical inspection method according to claim 11, wherein the electrical output signal of the photodetector is amplified and then distributed to a plurality of gate circuits in the same number as the plurality of illumination spots, each gate circuit is related to each of the illumination spots, and each output signal thus distributed is turned on/off based on the light detection control signal corresponding to each related illumination spot thereby to isolate and detect the scattered/diffracted/reflected light signal due to the scattered/diffracted/reflected light from each of the plurality of illumination spots.

15. The optical inspection method according to claim 11, wherein the electrical output signal of the photodetector is amplified and then distributed to a plurality of integrators in the same number as the plurality of illumination spots, each integrator is related to each of the illumination spots, and each output signal thus distributed is integrated only for a time zone when the light detection control signal corresponding to each illumination spot related to each integrator is in on state thereby to isolate and detect the scattered/diffracted/reflected light signal due to the scattered/diffracted/reflected light from each of the plurality of illumination spots.

16. The optical inspection method according to claim 1, wherein the plurality of the illumination spots are substantially aligned in substantially the same direction as the primary scanning of the sample stage on the surface of the sample.

17. The optical inspection method according to claim 1, wherein the plurality of the illumination spots are substantially aligned in substantially the same direction as the secondary scanning of the sample stage on the surface of the sample.

18. The optical inspection method according to claim 1, wherein the plurality of the illumination spots are substantially aligned in a predetermined direction at an angle to the direction of primary scanning of the sample stage between translation direction and the orthogonal direction on the surface of the sample.

19. The optical inspection method according to claim 1, wherein the illumination spots are arranged not in superposition on one another.

20. The optical inspection method according to claim 1, wherein the illumination spots are arranged substantially closely to each other.

21. The optical inspection method according to claim 1, wherein the illumination spots are arranged in positions superposed on one another at a predetermined ratio.

22. The optical inspection method according to claim 1, wherein the loci plotted by the illumination spots at the time of primary scanning of the sample stage are arranged substantially closely to each other.

23. The optical inspection method according to claim 1, wherein the loci plotted by the illumination spots at the time of primary scanning of the sample stage are superposed one on another at a predetermined ratio.

24. An optical inspection method for detecting a contaminant particle/defect existing on a surface or in an internal part near a surface of a sample to be inspected, using a sample stage for moving the sample in accordance with a predetermined pattern, an illumination unit for radiating a light from a light source on the surface of the sample and a light detection unit for detecting the light generated by the radiation of the illumination beam on the sample,
wherein the illumination unit includes a unit for splitting a single light flux emitted from the light source into a plurality of light fluxes, and a unit for forming a plurality of illumination spots by radiating the plurality of the light fluxes at predetermined discrete positions in predetermined spaced relation to each other on the surface of the sample,
wherein the light detection unit detects by isolating the light signal from each of the plurality of the illumination spots, and
wherein assuming that M and N are integers, a plurality of illumination spots in the number of M×N are divided into N groups of M illumination spots, the M illumination spots in each of the N groups are substantially aligned in substantially the same direction as primary scanning of the sample stage on the surface of the sample, and the N groups of the M illumination spots are substantially aligned in a predetermined direction at an angle to the direction of primary scanning of the sample stage between translation direction and orthogonal direction.

25. An optical inspection method for detecting a contaminant particle/defect existing on a surface or in an internal part near a surface of a sample to be inspected, using a sample stage for moving the sample in accordance with a predetermined pattern, an illumination unit for radiating a light from a light source on the surface of the sample and a light detection unit for detecting the light generated by the radiation of the illumination beam on the sample,
wherein the illumination unit includes a unit for splitting a single light flux emitted from the light source into a plurality of light fluxes, and a unit for forming a plurality of illumination spots by radiating the plurality of the light fluxes at predetermined discrete positions in predetermined spaced relation to each other on the surface of the sample,
wherein the light detection unit detects by isolating the light signal from each of the plurality of the illumination spots,
wherein assuming that M and N are integers, a plurality of illumination spots in the number of M×N are divided into N groups of M illumination spots, the M illumination spots in each of the N groups are substantially aligned in substantially the same direction as primary scanning of the sample stage on the surface of the sample, and the N groups of the M illumination spots are substantially aligned in a predetermined direction at an angle to the direction of primary scanning of the sample stage between translation direction and orthogonal direction, and
wherein the M illumination spots in each of the N groups are arranged in positions not superposed one on another, and the N groups of the M illumination spots are arranged in such a manner that the loci plotted by the illumination spots of each group at the time of primary scanning of the sample stage are located substantially closely to each other.

26. An optical inspection method for detecting a contaminant particle/defect existing on a surface or in an internal part near a surface of a sample to be inspected, using a sample stage for moving the sample in accordance with a predetermined pattern, an illumination unit for radiating a light from a light source on the surface of the sample and a light detection unit for detecting the light generated by the radiation of the illumination beam on the sample,
wherein the illumination unit includes a unit for splitting a single light flux emitted from the light source into a plurality of light fluxes, and a unit for forming a plurality of illumination spots by radiating the plurality of the light fluxes at predetermined discrete positions in predetermined spaced relation to each other on the surface of the sample,
wherein the light detection unit detects by isolating the light signal from each of the plurality of the illumination spots,
wherein assuming that M and N are integers, a plurality of illumination spots in the number of M×N are divided into N groups of M illumination spots, the M illumination spots in each of the N groups are substantially aligned in substantially the same direction as primary scanning of the sample stage on the surface of the sample, and the N groups of the M illumination spots are substantially aligned in a predetermined direction at an angle to the direction of primary scanning of the sample stage between translation direction and orthogonal direction, and wherein the M illumination spots in each of the N groups are arranged in positions not superposed one on another, and the N groups of the M illumination spots are arranged in such a manner that the loci plotted by the illumination spots of each group at the time of primary scanning of the sample stage are superposed one on another at a predetermined ratio.

27. The optical inspection method according to claim 1, wherein the scattered/diffracted/reflected light signal corresponding to the plurality of illumination spots isolated and detected are statistically processed thereby to improve the detection sensitivity of contaminant particles or defects.

28. An optical inspection method for detecting a contaminant particle/defect existing on a surface or in an internal part near a surface of a sample to be inspected, using a sample stage for moving the sample in accordance with a predetermined pattern, an illumination unit for radiating a light from a light source on the surface of the sample and a light detection unit for detecting the light generated by the radiation of the illumination beam on the sample, wherein the illumination unit includes a unit for splitting a single light flux emitted from the light source into a plurality of light fluxes, and a unit for forming a plurality of illumination spots by radiating the plurality of the light fluxes at predetermined discrete positions in predetermined spaced relation to each other on the surface of the sample, wherein the light detection unit detects by isolating the light signal from each of the plurality of the illumination spots, wherein assuming that M and N are integers, a plurality of illumination spots in the number of M×N are divided into N groups of M illumination spots, the M illumination spots in each of the N groups are substantially aligned in substantially the same direction as primary scanning of the sample stage on the surface of the sample, and the N groups of the M illumination spots are substantially aligned in a predetermined direction at an angle to the direction of primary scanning of the sample stage between translation direction and orthogonal direction, and wherein the scattered/diffracted/reflected light signal corresponding to the M illumination spots in each of the N groups isolated and detected are statistically processed thereby to improve the detection sensitivity of contaminant particles or defects.

29. The optical inspection method according to claim 1, wherein the distance covered by the secondary scanning between the present primary scanning and the next primary scanning is longer than the distance for inspection with a single illumination spot thereby to improve the speed of inspection of contaminant particles or defects.

30. An optical inspection method for detecting a contaminant particle/defect existing on a surface or in an internal part near a surface of a sample to be inspected, using a sample stage for moving the sample in accordance with a predetermined pattern, an illumination unit for radiating a light from a light source on the surface of the sample and a light detection unit for detecting the light generated by the radiation of the illumination beam on the sample, wherein the illumination unit includes a unit for splitting a single light flux emitted from the light source into a plurality of light fluxes, and a unit for forming a plurality of illumination spots by radiating the plurality of the light fluxes at predetermined discrete positions in predetermined spaced relation to each other on the surface of the sample, wherein the light detection unit detects by isolating the light signal from each of the plurality of the illumination spots, wherein assuming that M and N are integers, a plurality of illumination spots in the number of M×N are divided into N groups of M illumination spots, the M illumination spots in each of the N groups are substantially aligned in substantially the same direction as primary scanning of the sample stage on the surface of the sample, and the N groups of the M illumination spots are substantially aligned in a predetermined direction at an angle to the direction of primary scanning of the sample stage between translation direction and orthogonal direction, and wherein the scattered/diffracted/reflected light signal corresponding to the M illumination spots in each of the N groups isolated and detected are statistically processed and the distance covered by the secondary scanning between the present primary scanning and the next primary scanning is longer than the distance for inspection with a single illumination spot thereby to improve the speed of inspection of contaminant particles or defects.

31. An optical inspection apparatus for detecting a contaminant particle/defect existing on the surface or in the internal part near the surface of a sample to be inspected, comprising:

selected one of a sample stage adapted for first translation movement in primary scanning and second translation movement along the direction substantially orthogonal to the first translation movement in secondary scanning and a sample stage adapted for rotational movement in primary scanning and translation movement in secondary scanning;

a pulse laser source adapted for temporally repetitive pulse oscillation;

an illumination unit for radiating the pulse light from a light source on the surface of the sample; and a plurality of scattered/diffracted/reflected light detection units for detecting the radiated light scattered/diffracted/reflected on the sample in the direction at selected one of a plurality of elevation angles and a plurality of azimuthal angles on the one hand and combinations of the plurality of the elevation angles and the plurality of the azimuthal angles on the other hand, with respect to the sample surface;

wherein the illumination unit includes a unit for splitting a single light flux emitted from the pulse laser source into a plurality of light fluxes, a unit for radiating the plurality of the light fluxes at a plurality of discrete positions in a predetermined spaced relation with each other on the surface of the sample thereby to form a plurality of illumination spots;

the apparatus further comprising an optical signal isolation/detection unit for substantially aligning the plurality of illumination spots in substantially the same direction as the primary scanning of the sample stage on the sample surface while at the same time isolating and detecting the signals detected at different time points by the light detection unit from the light generated at the same position of the sample from a plurality of illumination spots.

32. An optical inspection apparatus for detecting a contaminant particle/defect existing on a surface or in an internal part near a surface of a sample to be inspected, comprising:
selected one of a sample stage adapted for first translation movement in primary scanning and second translation movement along a direction substantially orthogonal to the first translation movement in secondary scanning and a sample stage adapted for rotational movement in primary scanning and translation movement in secondary scanning;
a pulse laser source adapted for temporally repetitive pulse oscillation;
an illumination unit for radiating a pulse light from a light source on the surface of the sample; and
a plurality of scattered/diffracted/reflected light detection units for detecting the radiated light scattered/diffracted/reflected on the sample in a direction at selected one of a plurality of elevation angles and a plurality of azimuthal angles on the one hand and a plurality of combinations of the plurality of the elevation angles and the plurality of the azimuthal angles on the other hand, with respect to the sample surface;
wherein the illumination unit includes a unit for splitting a single light flux emitted from the pulse laser source into a plurality of light fluxes, and a unit for radiating the plurality of the light fluxes at a plurality of discrete positions in predetermined spaced relationship with each other on the surface of the sample thereby to form a plurality of illumination spots;
the apparatus further comprising an optical signal isolation/detection unit for substantially aligning the plurality of illumination spots on the sample surface in substantially the same direction as the secondary scanning of the sample stage while at the same time isolating and detecting the signals detected by the light detection unit based on the light generated from the plurality of illumination spots.

33. An optical inspection apparatus for detecting a contaminant particle/defect existing on a surface or in an internal part near a surface of a sample to be inspected, comprising:
selected one of a sample stage adapted for first translation movement in primary scanning and second translation movement along a direction substantially orthogonal to the first translation movement in secondary scanning and a sample stage adapted for rotational movement in primary scanning and translation movement in secondary scanning;
a pulse laser source adapted for temporally repetitive pulse oscillation; and
an illumination unit for radiating a pulse light from the light source on the surface of the sample; and
a plurality of scattered/diffracted/reflected light detection units for detecting the radiated light scattered/diffracted/reflected on the sample in the directions at selected one of a plurality of elevation angles and a plurality of azimuthal angles on the one hand and a plurality of combinations of the plurality of elevation angles and the plurality of azimuthal angles on the other hand, with respect to the surface of the sample;
wherein the illumination unit includes a unit for splitting a single light flux emitted from the pulse laser source into a plurality of light fluxes and a unit for radiating the plurality of the light fluxes at a plurality of discrete positions in predetermined spaced relation ship with each other on the surface of the sample thereby to form a plurality of illumination spots;
the apparatus further comprising an optical signal isolation/detection unit for substantially aligning the plurality of illumination spots in a predetermined direction at an angle of the sample surface to the direction of primary scanning of the sample stage between the direction of translation movement and the direction of orthogonal movement, and detecting by isolating the signals detected by the light detection unit based on the light generated from the plurality of the illumination spots.

34. An optical inspection apparatus for detecting a contaminant particle/defect existing on a surface or in an internal part near a surface of a sample to be inspected, comprising:
selected one of a sample stage adapted for first translation movement in primary scanning and second translation movement along a direction substantially orthogonal to the first translation movement in secondary scanning and a sample stage adapted for rotational movement in primary scanning and translation movement in secondary scanning;
a pulse laser source adapted for temporally repetitive pulse oscillation; and
an illumination unit for radiating a pulse light from a light source on the surface of the sample; and
a plurality of scattered/diffracted/reflected light detection units for detecting the radiated light scattered/diffracted/reflected on the sample in the directions at selected one of a plurality of elevation angles and a plurality of azimuthal angles on the one hand and a plurality of combinations of the plurality of elevation angles and azimuthal angles on the other hand, with respect to the sample surface;
wherein the illumination unit includes a unit for splitting a single light flux emitted from the pulse laser source into a plurality of light fluxes, and a unit for radiating the plurality of the light fluxes at a plurality of discrete positions at predetermined spaced relationship with each other on the surface of the sample thereby to form a plurality of illumination spots in the number of M×N (M, N: integers);
the apparatus further comprising an optical signal isolation/detection unit for splitting the plurality of illumination spots into N groups of M illumination spots, substantially aligning the M illumination spots in each of the N groups on the sample surface in substantially the same direction as the direction of primary scanning of the sample stage while at the same time aligning the N groups of the M illumination spots in a predetermined direction at an angle to the direction of primary scanning of the sample stage between the direction of translation and the direction orthogonal to the direction of translation, and detecting by isolating the signals detected by the light detection unit based on the light generated from the plurality of the illumination spots.

* * * * *